(12) United States Patent
Wax et al.

(10) Patent No.: US 12,171,524 B2
(45) Date of Patent: Dec. 24, 2024

(54) DEVICES, SYSTEMS, AND METHODS FOR IMAGING IN CERTAIN ENDOSCOPIC ENVIRONMENTS

(71) Applicants: DUKE UNIVERSITY, Durham, NC (US); THE UNIVERSITY OF NORTH CAROLINA AT CHAPEL HILL, Chapel Hill, NC (US)

(72) Inventors: Adam Wax, Durham, NC (US); Nicholas Shaheen, Durham, NC (US); Kengyeh Chu, Durham, NC (US); Derek Ho, Durham, NC (US); Zachary Steelman, Durham, NC (US)

(73) Assignees: DUKE UNIVERSITY, Durham, NC (US); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 437 days.

(21) Appl. No.: 17/589,333

(22) Filed: Jan. 31, 2022

(65) Prior Publication Data
US 2022/0240782 A1 Aug. 4, 2022

Related U.S. Application Data

(60) Provisional application No. 63/143,082, filed on Jan. 29, 2021.

(51) Int. Cl.
*A61B 5/00* (2006.01)
*A61B 1/018* (2006.01)
(Continued)

(52) U.S. Cl.
CPC ............ *A61B 5/0066* (2013.01); *A61B 1/018* (2013.01); *A61B 1/05* (2013.01); *A61B 1/0638* (2013.01);
(Continued)

(58) Field of Classification Search
CPC ......... A61B 1/05; A61B 10/04; A61B 1/0638; A61B 1/018; A61B 1/0014; G01B 9/02091
See application file for complete search history.

(56) References Cited

U.S. PATENT DOCUMENTS 8,496,574 B2 * 7/2013 Trusty ................ A61B 1/00135
396/17
8,679,003 B2 * 3/2014 Spivey ................ A61B 1/0014
600/153
(Continued)

OTHER PUBLICATIONS

Detection of intestinal dysplasia using angle-resolved low coherence interferometry, Journal of Biomedical Optics 16(10), 106002 (Oct. 2011) (Year: 2011).*
(Continued)

*Primary Examiner* — Oommen Jacob
(74) *Attorney, Agent, or Firm* — Quarles & Brady, LLP

(57) ABSTRACT

Systems and methods for multi-modal imaging using an endoscope having an instrument channel, where the imaging is achieved without using the channel, are disclosed. The systems can include a multi-modal imaging paddle housing couple to a distal end of the endoscope. The housing can receive at least two imaging probes. The imaging probes can be an angle-resolved low-coherence interferometry probe (a/LCI) and an optical coherence tomography (OCT) probe. The housing can be scaled and positioned to be visible via the endoscope camera. The system and method can include locating the housing in a region of interest using the endoscope camera, acquiring OCT measurements to identify targets, and then acquiring a/LCI measurements at the identified targets.

8 Claims, 7 Drawing Sheets

(51) Int. Cl.
    *A61B 1/05*     (2006.01)
    *A61B 1/06*     (2006.01)
    *A61B 1/07*     (2006.01)
    *A61B 10/04*     (2006.01)
    *A61B 18/00*     (2006.01)
    *A61B 18/14*     (2006.01)
    *G01B 9/02091*     (2022.01)

(52) U.S. Cl.
    CPC ............... *A61B 1/07* (2013.01); *A61B 10/04* (2013.01); *A61B 18/14* (2013.01); *G01B 9/02091* (2013.01); *A61B 2018/00577* (2013.01)

(56) References Cited

U.S. PATENT DOCUMENTS

| | | | | |
|---|---|---|---|---|
| 8,911,357 | B2 * | 12/2014 | Omori | A61B 1/00096 600/478 |
| 9,314,620 | B2 * | 4/2016 | Long | A61B 18/1206 |
| 9,335,154 | B2 * | 5/2016 | Wax | G01B 9/02044 |
| 9,545,290 | B2 * | 1/2017 | Tellio | A61B 90/11 |
| 9,615,748 | B2 * | 4/2017 | Tearney | A61B 5/0066 |
| 11,382,492 | B2 * | 7/2022 | Kawula | A61B 1/00066 |
| 11,547,277 | B2 * | 1/2023 | Steinberg | A61B 1/00101 |
| 2004/0059253 | A1 * | 3/2004 | Martone | A61B 10/04 600/564 |
| 2007/0201033 | A1 * | 8/2007 | Desjardins | G01B 9/02091 356/497 |
| 2009/0005638 | A1 * | 1/2009 | Zwolinski | A61B 17/00234 606/205 |
| 2009/0177094 | A1 * | 7/2009 | Brown | A61B 5/0066 606/2 |
| 2012/0101492 | A1 * | 4/2012 | Hancock | A61B 18/18 606/33 |
| 2013/0128264 | A1 * | 5/2013 | Wax | G01B 9/02022 356/300 |
| 2013/0135614 | A1 * | 5/2013 | Wax | G01J 3/453 356/451 |
| 2014/0153083 | A1 * | 6/2014 | Hakimi | H01S 5/5063 359/337.2 |
| 2016/0081656 | A1 * | 3/2016 | Abraham | A61B 8/582 600/439 |
| 2016/0256139 | A1 * | 9/2016 | Hadley | A61B 1/015 |
| 2016/0309993 | A1 * | 10/2016 | Hosogoe | A61B 1/00071 |
| 2017/0234675 | A1 * | 8/2017 | Iddan | G01B 9/02004 356/479 |
| 2019/0150720 | A1 * | 5/2019 | Altshuler | A61B 1/07 |
| 2019/0357883 | A1 * | 11/2019 | Steinberg | A61B 10/04 |
| 2020/0138274 | A1 * | 5/2020 | Aneja | A61B 10/04 |
| 2022/0240782 | A1 * | 8/2022 | Wax | G01B 9/02091 |

OTHER PUBLICATIONS

Analyzing spatial correlations in tissue using angle-resolved low coherence interferometry measurements guided by co-located optical coherence tomography, Apr. 2016 | vol. 7, No. 4 Biomedical Optics Express 1400 (Year: 2016).*

Design and validation of an angle-resolved low-coherence interferometry fiber probe for in vivo clinical measurements of depth-resolved nuclear morphology, Journal of Biomedical Optics 16(1), 011003 (Jan. 2011) (Year: 2011).*

Kendall et al., "Prospective detection of cervical dysplasia with scanning angle-resolved low coherenc interferometry," Biomedical Optics Express, vol. 11, No. 9, Sep. 1, 2020.

Wojtkowski, M., et al., Ultrahighresolution, high-speed, Fourier domain optical coherence tomography and methods for dispersion compensation. Optics express, 2004. 12(11): p. 2404-2422.

* cited by examiner

DEVICES, SYSTEMS, AND METHODS FOR IMAGING IN CERTAIN ENDOSCOPIC ENVIRONMENTS

CROSS-REFERENCE TO RELATED APPLICATIONS

This application is related to, claims priority to, and incorporates by reference herein for all purposes U.S. Provisional Patent Application No. 63/143,082, filed Jan. 29, 2021.

STATEMENT REGARDING FEDERALLY FUNDED RESEARCH

This invention was made with Government support under Federal Grant nos. 1R01 CA 16721 and R01 CA210544 awarded by the NIH. The Federal Government has certain rights to this invention.

BACKGROUND

Upwards of 90% of all cancers originate in the epithelium. There are two reasons for this prevalence. First, epithelium is the body's barrier to the environment so any contact with an environmental carcinogen will be felt there first. Second, the nature of epithelium is such that there is constant turnover of cells as the tissue refreshes itself, offering a greater chance for cell proliferation to go awry. Monitoring epithelial tissues for signs of pre-cancerous growth can be a challenge since it presents such a large area and evidence of aberrant growth is not always apparent.

Angle-resolved low coherence interferometry (a/LCI) is a technology that was developed to help assess the health of epithelial tissues by measures the size of cell nuclei in sub-surface layers. In particular, pre-cancerous growth, i.e., dysplasia, is characterized by enlargement of cell nuclei, specifically in the basal layer of the epithelium where cell division occurs as new cells are generated. s/LCI has been demonstrated in human patients in vivo to be a sensitive and specific means of detecting dysplasia in both the cervix and the esophagus.

The a/LCI technique determines the size of particles in a sample by measuring the scattering of light as a function of depth and angle, and computing the size and density of scatterers from the angle resolved scattering distribution. The biomedical applications of a/LCI include the detection of cancer and precancer, which are often characterized by enlarged cell nuclei that are detectable by a/LCI.

Previous implementations of a/LCI have been constrained by the limited sampling scope of the first a/LCI devices, typically a fiber-optic probe which could sample a single, small point, less than a millimeter in diameter, but required manual repositioning to sample additional points.

A need exists for imaging systems and methods that facilitate the use of a/LCI without the above-references shortcomings. A need exists for imaging systems and methods that can acquired images via a/LCI or other imaging modalities without using the instrument channel of an endoscope. A need exists for imaging systems and methods that provide for rough identification of targets via visualization, intermediate identification of targets via one or more imaging methods, and specific identification of targets via a/LCI. More broadly, a need exists for imaging systems and methods where a clinician can identify a potential target, image the target to determine if a biopsy is needed, and acquire a biopsy sample of the target in a single process that does not involve removing or re-inserting an endoscope or removing and re-inserting or replacing tools within the instrument channel of the endoscope.

SUMMARY

The present disclosure is based, in part, on the goal to enable, automated analysis of broad areas of epithelial tissue for evidence of pre-cancerous dysplasia. The approach is to use a wide area tissue imaging approach, based on coherence gating where depth resolved tissue information is obtained at the micron scale, to identify suspicious areas combined with a high-resolution technique that can identify the presence of dysplasia with high accuracy. This builds upon previous work using angle-resolved low coherence interferometry (a/LCI) which uses light scattering methods to determine the size of cell nuclei in a probed area of tissue. To enable broad tissue surveillance with a/LCI, one aspect of the present disclosure provides devices, systems, and methods of combining the approach with another imaging modality. Several proposed combinations are described which include a/LCI with multiplexed LCI (mLCI) and with different embodiments of optical coherence tomography (OCT).

In an aspect, the present disclosure provides a system for multi-modal imaging using an endoscope having an instrument channel, wherein the multi-modal imaging is achieved without using the instrument channel. The system includes an endoscope, a multi-modal imaging paddle housing, an angle-resolved low-coherence interferometry (a/LCI) probe, an optical coherence tomography (OCT) probe, and an imaging controller. The endoscope is selected from the group consisting of an anoscope, a colonoscope, a colposcope, an esophagoscope, a gastroscope, a laryngoscope, and a sigmoidoscope. The endoscope has a video camera positioned at a distal end for providing video images. The multi-modal imaging paddle housing is coupled to the distal end of the endoscope. The multi-model imaging paddle housing occupies a retracted position adjacent to the distal end of the endoscope. The multi-modal imaging paddle housing is optionally adapted to be movable between the retracted position and an extended position that is extended axially and/or radially from the distal end of the endoscope. The multi-modal imaging paddle housing is adapted to receive a portion of at least two imaging probes. The multi-modal imaging paddle housing has a single imaging window, through which each of the at least two imaging probes acquires images, or two imaging windows, each through which a respective one of the at least two imaging probes acquires images. The a/LCI probe has at least a distal portion received within the multi-modal imaging paddle housing. The OCT probe has at least a distal portion received within the multi-modal imaging paddle housing. The imaging controller is operatively coupled to the a/LCI probe and the OCT probe. The multi-modal imaging paddle housing has a shape and a location in the retracted position. The shape and the location combine to make the multi-modal imaging paddle housing visible in the video images provided by the video camera, such that a user can visually guide the multi-modal imaging paddle housing to a region of interest. The a/LCI probe and the OCT probe are electronically couples to the imaging controller and optically coupled to respective light sources and optical detectors via wires and optical fibers that are coupled to an exterior surface of the endoscope. The a/LCI probe operates within a first wavelength range. The OCT probe operates in a second wavelength range. The first and second wavelength ranges are different and non-overlapping. The single imaging window transmits at least 95% of light at each wavelength in the first wavelength range and the second wavelength range. One of the two imaging windows transmits at least 95% of light at each wavelength in the first wavelength range and the other of the two imaging windows transmits at least 95% of light at each wavelength in the second wavelength range. The instrument channel is not occupied by the a/LCI probe or the OCT probe.

In another aspect, the present disclosure provides a method of using an endoscope having an instrument channel with multi-modal imaging that does not occupy the instrument channel. The method includes: a) visually guiding the endoscope to a region of interest via video images secured via the endoscope, wherein a multi-modal imaging paddle housing that is coupled to a distal end of the endoscope is visible in the video images; b) optionally deploying the multi-modal imaging paddle housing from a retracted position to an extended position; c) acquiring OCT measurements over the region of interest to identify locations of interest, wherein the acquiring is performed by an OCT probe having at least a distal portion received within the multi-modal imaging paddle housing, wherein the locations of interest are identified by analyzing the OCT measurements; d) acquiring a/LCI measurements at the locations of interest to identify one or more targets, wherein the acquiring is performed by an a/LCI probe having at least a distal portion received within the multi-modal imaging paddle housing, wherein the one or more targets are identified by analyzing the a/LCI measurements; and e) optionally either: ablating the one or more targets or acquiring a biopsy sample from the one or more targets, wherein the optional ablating is optionally not performed via the instrument channel.

In yet another aspects, the present disclosure provides an endoscope attachment that facilitates multimodal imaging. The attachment includes a multi-modal imaging paddle housing and a coupling cuff. The multi-modal imaging paddle housing is adapted to receive at least two imaging probes. The multi-modal imaging paddle housing has a single imaging window, through which at each of the at least two imaging probes acquire images, or two imaging windows, each through which a respective one of the at least two imaging probes acquires images. The coupling cuff is affixed to the multi-modal imaging paddle housing and is adapted to couple the housing to a distal end of an endoscope. The single imaging window transmits at least 95% of light at each wavelength in a first wavelength range and a second wavelength range. One of the two imaging windows transmits at least 95% of light at each wavelength in the first wavelength range and the other of the two imaging windows transmits at least 95% of light at each wavelength in the second wavelength range.

DETAILED DESCRIPTION

Before the present invention is described in further detail, it is to be understood that the invention is not limited to the particular embodiments described. It is also understood that the terminology used herein is for the purpose of describing particular embodiments only and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

As used herein, "non-overlapping" when used in reference to a range of wavelengths of light means that less than 5%, less than 3%, less than 1%, or less than 0.1% of photons or optical intensity within two given wavelength ranges are from a wavelength sub-range that overlaps. In other words, as used herein, non-overlapping wavelength ranges can include up to 0.1%, up to 1%, up to 3%, or up to 5% overlap in terms of the number of photons or optical intensity at a given overlapping range.

In one aspect, the present disclosure provides a system for multi-modal imaging using an endoscope having an instrument channel. The multi-modal imaging is achieved without using the instrument channel.

Figure 1:
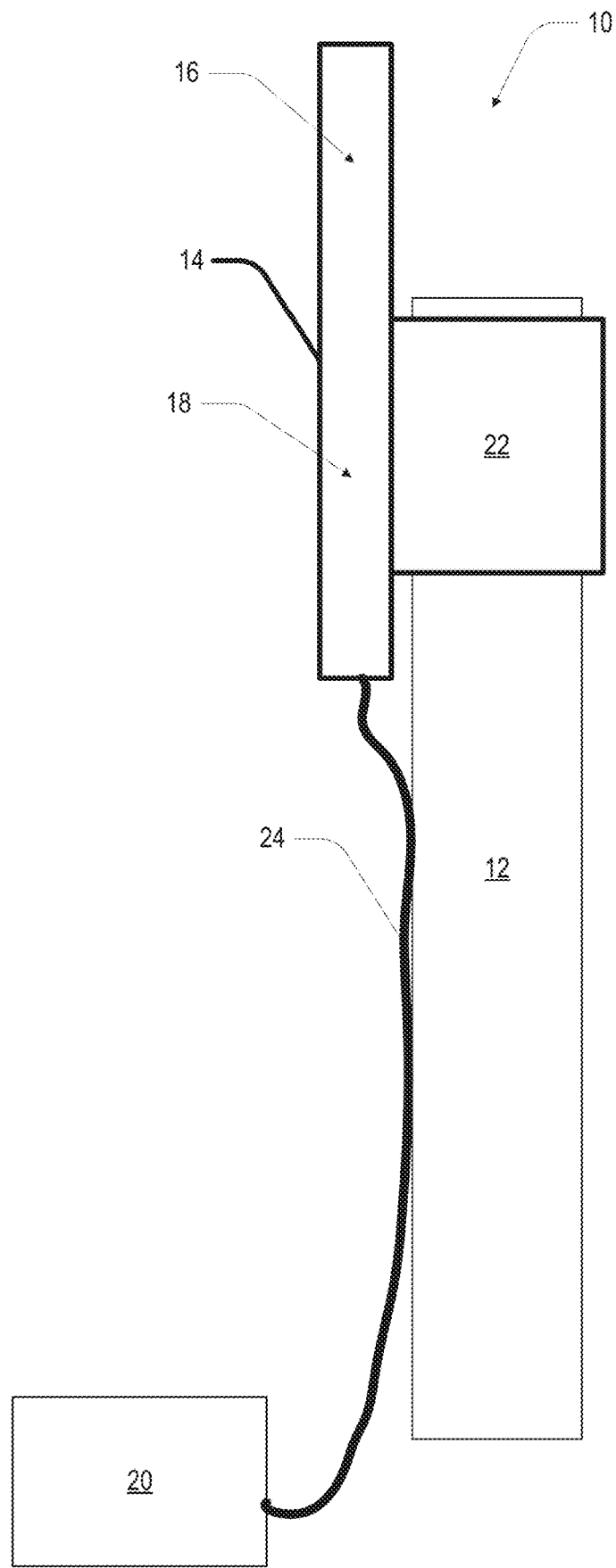
FIG. 1 is a schematic of a system, in accordance with aspects of the present disclosure.

Referring to FIG. 1, the system 10 includes an endoscope 12, a multi-modal imaging paddle housing 14, an angle-resolved low-coherence interferometry (a/LCI) probe 16, an optical coherence tomography (OCT) probe 18, and an imaging controller 20. In the illustrated aspect, the housing 14 is affixed to the endoscope via a flexible cuff 22, though other coupling mechanisms are contemplated. The a/LCI probe 16 and the OCT probe 18 are electronically coupled to the imaging controller and optically coupled to respective light sources and optical detectors via wires and optical fibers 24 that are coupled to an exterior surface of the endoscope 12.

The endoscope 12 is selected from the group consisting of an anoscope, a colonoscope, a colposcope, an esophagoscope, a gastroscope, a laryngoscope, and a sigmoidoscope. Without wishing to be bound by any particular theory, certain endoscopes are not useful with the present disclosure, because they navigate passageways that are too narrow to facilitate the multi-modal imaging paddle housing 14. One example is a bronchoscope, which is expressly excluded from the list of endoscopes disclosed herein. The endoscope 12 has a video camera positioned at a distal end for providing video images. The endoscope 12 includes an instrument channel. The instrument channel is not occupied by the a/LCI probe 16 or the OCT probe 18.

Figure 2:
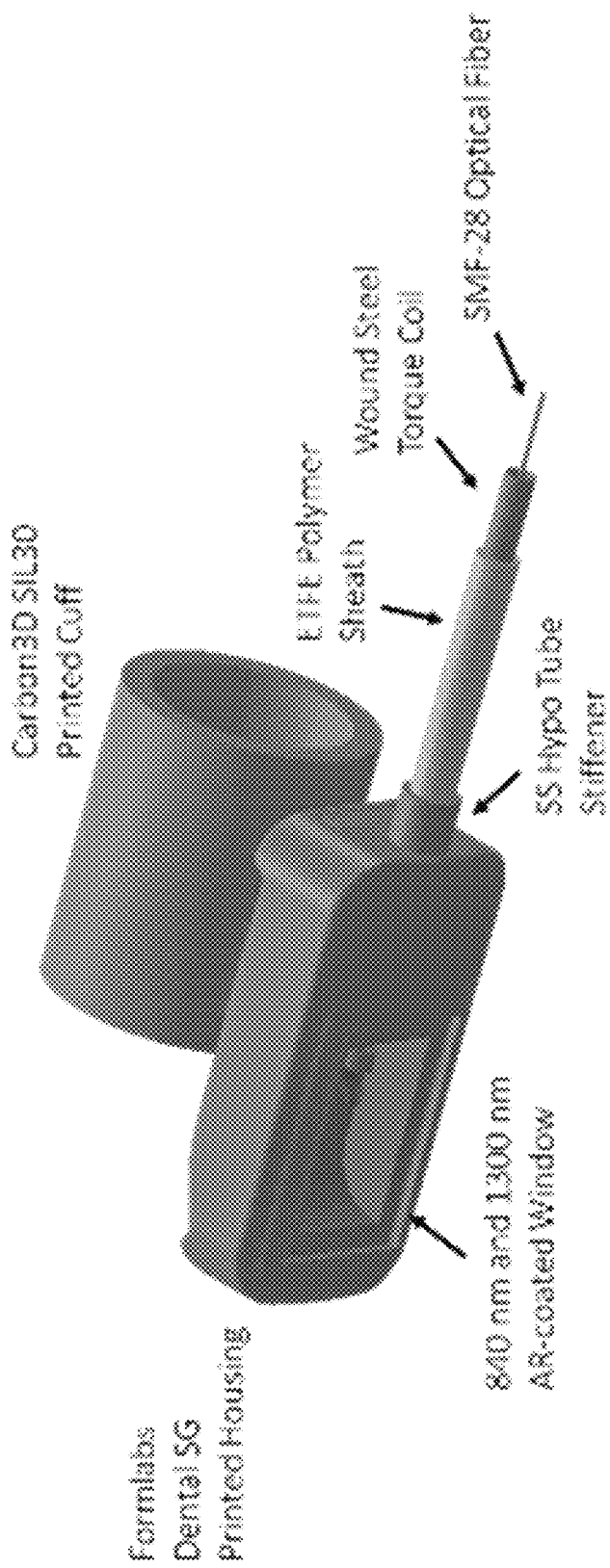
FIG. 2 is a schematic of an endoscope attachment with a multi-modal imaging paddle housing, in accordance with aspects of the present disclosure.
Figure 3:
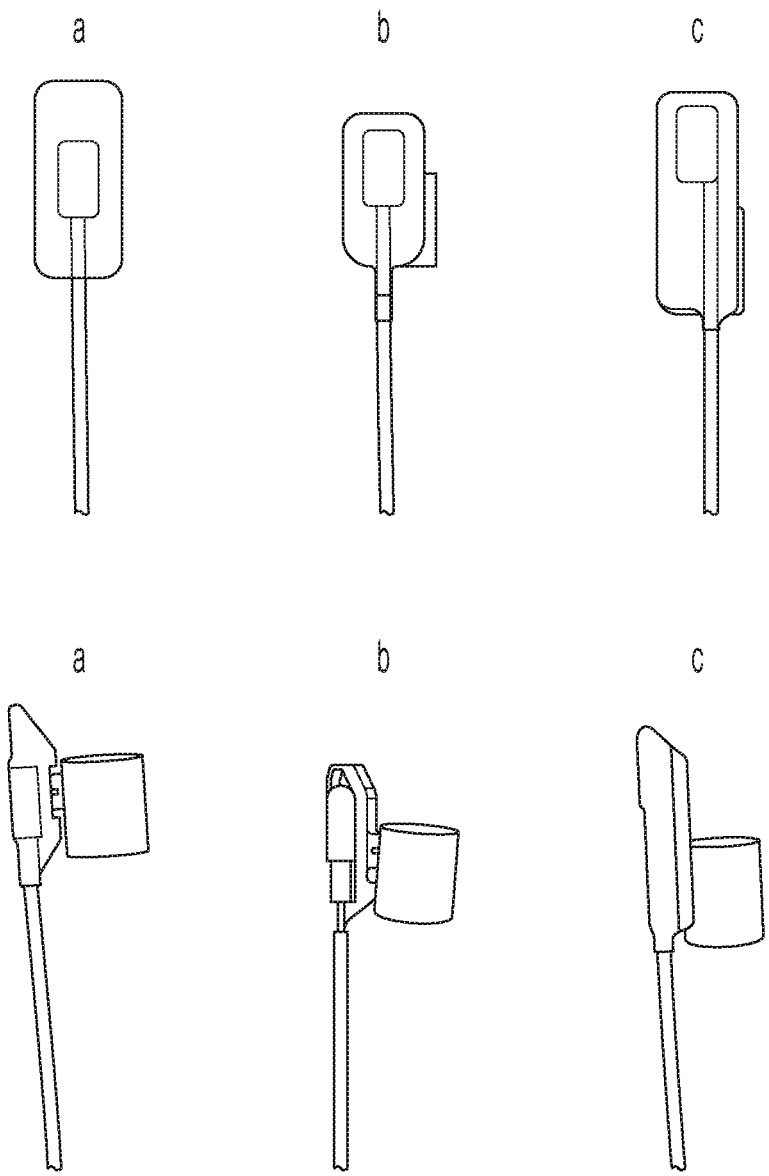
FIG. 3 shows images of multiple paddle designs, in accordance with aspects of the present disclosure.

Referring to FIG. 2, a closer view of one aspect of the multi-modal imaging paddle housing 14 is illustrated. The housing 14 can include a flexible cuff 22. The housing 14 is adapted to receive a portion of at least two imaging probes, including in some cases the a/LCI probe 16 and OCT probe 18 discussed herein. Referring to FIG. 3, multiple variations on the design of the housing 14 are shown. Those denoted by letters 'a' and 'b' have room for one probe and those denoted by the letter 'c' has room for two probes, as described above.

The illustrated aspect shows one transmission window, but two (or more) transmission windows are expressly contemplated, and a skilled artisan will recognize how to orient two (or more) transmission windows to be functional and effective. In the one transmission window embodiment, the single imaging window transmits at least 95% of light at each wavelength in the first wavelength range and the second wavelength range. In the two transmission window embodiment, one of the two imaging windows transmits at least 95% of light at each wavelength in the first wavelength range, and the other of the two imaging windows transmits at least 95% of light at each wavelength of the second wavelength range. In other words, one window is for use with the a/LCI probe and the other window is for use with the OCT probe.

Figure 4:
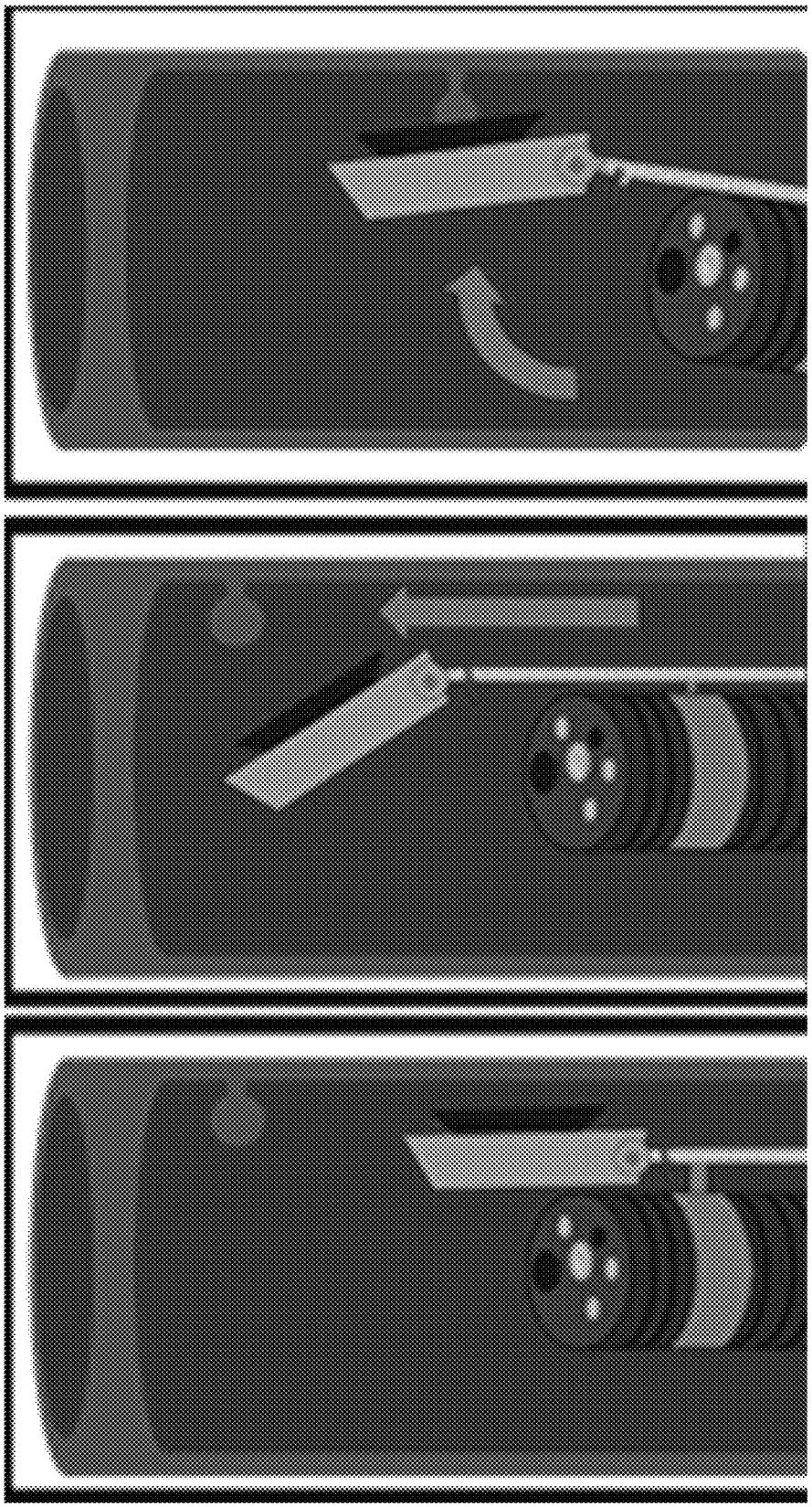
FIG. 4 is a schematic representation of mechanical actuation of the multi-modal imaging paddle housing, in accordance with aspects of the present disclosure.

The multi-modal imaging paddle housing 14 can be movable between a retracted position and an extended position. The system 10 can include various mechanical actuators and/or motors and/or other physical means of moving the paddle housing 14, as would be appreciated by a skilled artisan in the biomechanical arts. In some cases, a flexible cuff 22 can be affixed to an actuator which itself is affixed to the housing 14, thereby providing the housing 14 with the capability of moving and being affixed to the endoscope 12 via a flexible cuff 22. In some cases, the housing 14 is affixed to a mechanical actuator, which itself is affixed to the endoscope via temporary or permanent connections. Referring to FIG. 4, an illustration of an embodiment including a mechanical actuator is shown. The left image shows the housing 14 in the retracted position. The middle panel shows the housing 14 in the extended position. The right panel shows the housing 14 being moved by virtue of movement of the endoscope.

The housing 14 can include the capability to radiofrequency ablate tissue by way of one or more radiofrequency ablation electrodes. These electrodes are coupled to external power and control via the wires that run along the exterior of the endoscope.

The housing 14 can adopt a variety of physical conformations. In one specific aspect, the housing 14 has a relatively long and thin profile, such that a length of the housing is at least three times greater than a thickness of the housing (in some cases, thickness is measured radially relative to the orientation of the endoscope 12). In some aspects, this shape profile can help facilitate imaging while maintaining a relatively low profile relative to the size and shape of the endoscope itself. The housing has a shape and a location relative to the endoscope 12 when the housing 14 is in the retracted position. In some cases, the shape and position combine to make the housing 14 visible in video images provided by the video camera of the endoscope The a/LCI probe 16 has at least a distal portion received within the multi-modal imaging paddle housing 14. The a/LCI probe operates within a first wavelength range. The first wavelength range includes 840 nm within it. Example wavelength is 835 nm with −3 dB bandwidth of 40 nm.

In certain cases, for certain applications, such as those involving a colposcope or similar, the a/LCI probe can include a reflection-only three-optical rotator (ROTOR) prism and a two-axis scanning mirror. In these cases, the controller can be adapted to direct the a/LCI probe and respective light sources and detectors to acquire A-scans by varying an angle of the ROTOR prism.

The a/LCI probe can be coupled to respective light sources and optical detectors via a pathlength-matched linear fiber array. The array can include a plurality of single-mode optical fibers, coherent fiber bundles, or a single multi-mode fiber.

The OCT probe 18 has at least a distal portion received within the multi-modal imaging paddle housing 14. The OCT probe 18 operates within a second wavelength range. The second wavelength range includes 1310 nm with in it. Example bandwidth has a 1318 nm center wavelength with a −3 dB bandwidth of 83 nm.

In some cases, the OCT probe 18 is a rotating probe.

The first wavelength range and the second wavelength range are different. The first wavelength range and the second wavelength range are non-overlapping.

The system can include respective light sources and optical detectors for the function of the a/LCI probe 16 and the OCT probe 18. A skilled artisan will recognize which light sources and optical detectors may be suitable for use with these imaging modalities. Light sources can include superluminescent diodes, filtered light from a supercontinuum source or light from a femtosecond pulsed laser. Detectors can include spectrometers which resolve the signal by wavelength for detection using a linescan CCD or CMOS array.

The imaging controller 20 can be any computer, processor, or other computing device that is either generally or specifically programmed to be usable with an a/LCI system for acquiring a/LCI data. The imaging controller 20 can also be generally or specifically programmed to be usable with an OCT system for acquiring OCT data. A skilled artisan will recognize that a wide variety of possibilities exist for controllers suitable for acquiring the data as described herein.

The imaging controller 20 is operatively coupled to the a/LCI probe 16 and the OCT probe 18.

In another aspect, the present disclosure provides an endoscope attachment that facilitates multimodal imaging. The attachment includes the multi-modal imaging paddle housing and a coupling cuff, as described above.

In another aspect, the present disclosure provides a method of using an endoscope. The endoscope has an instrument channel. The multi-modal imaging does not occupy the instrument channel. The method includes: a) visually guiding the endoscope to a region of interest via video images secured via the endoscope, wherein a multi-modal imaging paddle housing that is coupled to a distal end of the endoscope is visible in the video images; b) optionally deploying the multi-modal imaging paddle housing from a retracted position to an extended position; c) acquiring OCT measurements over the region of interest to identify locations of interest, wherein the acquiring is performed by an OCT probe having at least a distal portion received within the multi-modal imaging paddle housing, wherein the locations of interest are identified by analyzing the OCT measurements; d) acquiring a/LCI measurements at the locations of interest to identify one or more targets, wherein the acquiring is performed by an a/LCI probe having at least a distal portion received within the multi-modal imaging paddle housing, wherein the one or more targets are identified by analyzing the a/LCI measurements; and e) optionally either: ablating the one or more targets or acquiring a biopsy sample from the one or more targets, wherein the optional ablating and the optional acquiring are not performed via the instrument channel.

In some cases, step b) is not optional.

In some cases, step e) is not optional. In some cases, the method includes ablating the one or more targets at step e). The ablating can be achieved via one or more radiofrequency ablation electrodes located on an exterior surface of the multi-modal imaging paddle housing. In some cases, the method includes acquiring a biopsy sample from the one or more targets. The acquiring the biopsy sample can be achieved via the instrument channel of the endoscope.

The acquiring of steps c) and d) can use the parameters described elsewhere herein.

The present disclosure provides, in part, devices, systems and methods to expand the area of epithelial tissue probed by a/LCI. Reaching this aim has been challenging since the optical geometry required for a/LCI has unique constraints compared to typical optical systems. a/LCI necessarily must collect light scattered across a large range of angles (large aperture) to analyze angle dependent scattering. However, the incident light in a/LCI must also have a relatively large spot on the sample. The large spot is needed to ensure that a sufficient number of scattering centers (cell nuclei) are examined in each scan but also to ensure that the angular distribution of incident light is narrow. If the incident beam is focused too tightly, the incident light arrives at many angles and smears out the distribution of scattered light as previously described.

Another instrumentational aspect that is required to enable clinical usage of a/LCI is a method to allow targeting of the modality. The a/LCI method is high resolution in that it obtains information about cell nuclei at the sub-micron scale across a relatively small field of view. Although a scanning method could be used to comprehensively scan wide tissue areas, this is not likely to be effective since each a/LCI scan can take 10-200 milliseconds to process. Thus, a wide area scan would be prohibitively long to implement during a single procedure. Instead, the devices, systems and methods according to the present disclosure seek to target a/LCI measurements to specific locations which are identified using another imaging modality, such as Optical Coherence Tomography (OCT), as a 'red flag' technology. Hence, one aspect of the present disclosure provides devices, systems and methods for scanning an a/LCI beam followed by implementations that combine wide area scanning at lower resolution with localized a/LCI high resolution measurements of nuclear morphology.

a/LCI Scanning

The inventors have previously described a system that enables scanning of an a/LCI beam. This method for scanning an a/LCI beam across a sample preserves the 1) angle of incidence, 2) collected angular range of scattered light and 3) a compact form factor compatible with endoscopic imaging. The approach produces radial a/LCI scans using a reflection-only three-optic rotator (ROTOR) prism and a two-axis scanning mirror. The ROTOR was designed to simultaneously rotate the illumination beam and collection data about the optic axis. A two-axis scanning mirror was then employed to scan the illumination beam perpendicularly to the collection axis, producing an "asterisk"-shaped scanning profile. Characterization of the scanning nature of the system was performed using polystyrene microsphere phantoms.

In one embodiment, the scanning a/LCI system was constructed using a previously developed clinical a/LCI engine and probe. Briefly, light from a superluminescent diode (Superlum SLD-MS, 1=830 nm, FWHM=20 nm) is P-polarized using a polarization controller and propagated to the distal end of the probe using a polarization-maintaining (PM) fiber. Light from the PM fiber is collimated by a GRIN lens onto the sample plane, producing elastic scattering. The PM fiber is offset from the optical axis, resulting in the collimated beam reaching the sample at an oblique angle. The elastically scattered light from the sample is relayed by the GRIN onto a coherent fiber bundle (Schott Inc., Southbridge, MA), mapping angular scattering to individual elements within the bundle. The face of the proximal end of the bundle is then relayed to the slit of an imaging spectrograph (SP-2150i, Princeton Instruments, Acton, MA) where it is overlapped with a reference field and detected with a scientific-grade CCD camera (PIXIS: 100, Trenton, NJ) to enable coherence-gated depth sectioning.

In another embodiment, the scanning a/LCI system extends the sample plane of the clinical a/LCI system using two symmetric 4f lens relays, with $f_1$, $f_4$=30 mm and $f_2$, $f_3$=100 mm. This allows for incorporation of the ROTOR prism and scanning mirror. The ROTOR prism is composed of three mirrors which rotate as a unit relative to the optical axis. Two on-axis elliptical mirrors are oriented at 55° using a custom 3D-printed mount, while a third mirror is held 6 cm from the optic axis in a right-angle cage system. This entire structure is then mounted on two 30 mm rotation mounts, which allow rotation of the entire assembly over a full 360°. Similar in principle to a Dove prism, a rotation of the ROTOR prism over a given angle results in a rotation of the excitation beam and collection axis at twice that angle. By employing radial scans across a 180° range a circular region on the image plane can be characterized. Thus, the maximum required rotation of the ROTOR is only 90°.

In another embodiment, a gimbal-mounted two-axis scanning mirror was incorporated at the distal end of the system to scan the illumination beam perpendicular to the collection axis. Using this configuration, tilting of the scanning mirror produces a line-scan on the image plane. This line may then be rotated around the optical axis using the ROTOR prism, and the two-axis mirror can be tilted in a different direction to perform another line-scan with its orientation set by twice the rotation angle of the prism, maintaining a right angle with the collection axis. Repeating this method over different rotation angles of the ROTOR produces an asterisk-shaped scanning profile capable of reaching any point within a circle, with its diameter determined by the maximum linear scanning range. In this way, scanning a/LCI produces a two-dimensional map of depth-resolved angular scattering profiles.

a/LCI image processing has been described previously. Briefly, four exposures were taken during each scan (total, sample, reference, and dark fields) to isolate the interferometric term in the acquisition. Each background-subtracted a/LCI scan is a two-dimensional map, composed of an interferogram for each scattering angle. The wavelength axis of each interferogram was first converted to wavenumber ($k=2\pi/\lambda$), and resampled to be linear in k. Second-order dispersion compensation was performed digitally, followed by a Fourier-transform to produce a map of scattering intensity for each scattering angle as a function of sample depth. For each acquisition in this study, a total of ten a/LCI scans were averaged to improve SNR. Each a/LCI scan was averaged over ~480 mm of depth to produce a single angular scattering profile.

The system according to this embodiment was validated for two-dimensional scanning using a 3×3 array of microsphere phantoms. Phantoms with sphere with diameters of 6, 10, and 15 mm were arranged in a unique pattern (10 mm on the corners, 6 mm at the edges, and 15 mm in the center) to create a sample with spatially varying scattering features. Three samples were taken along a scan line at intervals of 5 mm (−5 mm, 0 mm, and +5 mm from the optic axis) to collect one sample from each unique phantom area within the middle row of the 3×3 array. The scan line was then rotated using the ROTOR prism, and the linear scan was repeated. The prism was positioned at 0°, 45°, and ±22.5° to achieve a rotation of the scanning axis of 0°, 90°, and ±45°. This produces a single sample point from each phantom cube in the array. The center point was resampled in each scan, though no deviation in the size measurement was observed.

Each phantom was correctly identified with sub-wavelength precision. Mean error was—2.9%, with a maximum error of 6.7% (lower middle, 6 mm spheres were identified as 5.6 mm). Maximum absolute error was 0.8 mm, though this was on a large sphere size (15 mm) resulting in a percentage error of only 5.3%.

Each radial scan was performed over a 1 cm range, to fit within the measured 12 mm scan range while sampling each point within the 3×3 phantom grid. At each point, determination of the sphere size with sub-wavelength accuracy was observed. Mean absolute error was 0.26 mm.

Single Mode Fiber a/LCI Probe.

Previous a/LCI devices have utilized optical fiber bundles to relay angular scattering from the tissue surface back to the optical engine. Several different types of imaging bundles have been explored for their use in coherent imaging. Although an optical fiber can support many modes of transmission, it is only the fundamental mode that is most suited for coherence imaging. Unfortunately, there are no available commercial options for single mode fiber bundles. Instead, a/LCI has previously used a fiber bundle consisting of step index fibers which allow multiple modes to propagate but since they have different effective group velocities, a sufficiently long fiber bundle (>1-2M) will allow them to be separated by propagation time using a coherence gate. The most successful a/LCI probe used a leached imaging fiber bundle, where multiple fibers embedded in a matrix are drawn in parallel and then the matrix is leached away, leaving multiple individual step-index fibers. Leached imaging bundles are expensive (>$1,000/meter), very lossy (10-20% transmission per meter in the near-infrared) and fragile, caused by the loose step index fiber elements on the order of 6-12 mm. Since these bundles allow multiple modes to propagate, all but the fundamental mode are effectively contributing to a noisy background. However, the nature of the bundled independent elements also serves to reduce cross talk, i.e. coherent coupling, between the fibers. Less expensive imaging bundles exhibit poor pathlength stability, as well as poor flexibility and substantial cross talk, making them impractical for coherent imaging.

As an alternative to using a commercial imaging bundle, one embodiment of the present disclosure provides a pathlength-matched linear fiber array (PLFA) using single-mode (SM) fibers and a 3D-printed ferrule. The PLFA allows for single-mode propagation with high throughput (>99.93%/meter), while maintaining flexibility and significantly reducing component cost as single mode fibers are much less expensive than imaging bundles. To improve angular sampling, another embodiment of the present disclosure utilizes a distal probe body comprising of a miniature 4f lens system was designed to demagnify the fiber array image onto the back focal plane of a gradient-index (GRIN) lens. A gold-coated right-angle prism was placed before the GRIN lens to permit side-viewing, a significant advantage for imaging in the upper GI tract. This probe represents the first a/LCI device with this functionality. All distal optics are held together in a custom 3D-printed housing, whose outer diameter can be tailored to be compatible with a range of endoscopic applications. The result is a flexible, side-viewing a/LCI probe with high throughput which uses cheap, standardized optical components. Use of this device will allow for rapid, biopsy-free screening for precancer in the esophagus.

In one embodiment, the PLFA comprises 30 or more single-mode fibers aligned in a linear configuration and matched in optical pathlength to very high precision. Interferometer measurements are used to precisely characterize the optical pathlength of SM fiber to a sensitivity of ~5 mm. Bare fibers were connectorized and polished on an automated polishing tower (KrellTech) for ~15 seconds using a 6 mm grit polishing film, creating a surface smooth enough to allow light to propagate. The bare fiber was then inserted into the interferometer to examine its optical pathlength. If found to be too long, the fiber was removed from the interferometer, and again a small portion just visible to the naked eye was pushed out of the adapter and re-polished. It was found empirically that this process can remove optical pathlength in increments of 30-70 mm. Polishing and pathlength inspection were repeated for 30 fibers, until each 2.5-meter fiber was matched to within ±50 mm, representing a normalized length precision of $\pm\lambda L/l=0.002\%$. Each fiber was marked near the tip with black ink in case a breakage rendered it unusable, and set aside for later use.

To assemble the fibers, one embodiment of the present disclosure provides a ferrule for tight lateral packing. To avoid expensive precision-machined parts, a plastic ferrule was designed and printed on a stereolithography-type 3D printer (Form2, Formlabs) which exhibits excellent z-resolution of 25 mm. Two ferrule halves (4.4×2×10 mm) were designed and printed with a 50 mm by 3.2 mm depression on one side, which corresponded to a 100 mm by 3.2 mm linear slot once the two halves were aligned. Two access channels were added to one side of the ferrule to help pack down the fibers during assembly.

The ferrule halves were held together with a thin strip of adhesive tape and placed in a fixture for fiber insertion. A glass coverslip acted as a backstop for the fiber, and an inspection camera with a 14-megapixel Panasonic sensor was positioned on the other side of the coverslip to monitor the fiber placement process.

In a/LCI, it is important to control the polarization of the illumination beam. To that end, the first and last fiber inserted into the ferrule is a polarization-maintaining (PM) fiber (HB800G, Thorlabs), which is polished using a bare-fiber adaptor to reveal the stress rods. The PM fiber is rotated to align its slow axis with the fiber array, the rotation angle can be controlled manually with an accuracy of <5°. After insertion of the PM fiber, each of the 30 pathlength-matched fibers was inserted in turn, and an additional PM fiber inserted and aligned at the opposite end in case the primary PM fiber failed mechanically during assembly. Once all fibers were inserted, a single drop of low-viscosity optical adhesive (Norland NOA 72) was placed into the access channel of the ferrule, and allowed to spread between the fibers. The adhesive was spot-cured using a UV gun (LOC-TITE EQ CL32), and additional epoxy was added and cured to protect the stripped ends of the fibers proximal to the ferrule. The insertion and curing process was repeated for all 30 fibers in order (excluding the two PM fibers) to construct the proximal end of the PLFA.

To enable use of the PLFA to detect angular scattering, a distal probe body was constructed using miniature lenses and a right-angle prism. Previous a/LCI instruments have used a single gradient-index (GRIN) objective lens placed in direct contact with the fiber bundle. In one embodiment of present disclosure, additional relay lenses are used to demagnify the array of fibers since our SM fibers span—2.4 mm, and GRIN lenses are typically less than 2.0 mm in diameter. To achieve this a 4f imaging system is used consisting of an achromat (Edmund Optics, f=7.5 mm) and a molded glass asphere (Thorlabs, f=4.03 mm) producing a magnification of 0.54. A gold-coated right-angle prism (Thorlabs, 3 mm) was used to reflect light between the molded aspheric lens and the GRIN lens for side viewing. The GRIN lens (1.8 mm diameter, pitch=0.23, Edmund Optics) was used to collimate the illumination beam at an oblique angle onto the sample. Scattered light from the sample is then collected along the same optical train, such that each scattering angle is mapped onto a discrete fiber in the PLFA.

Figure 5:
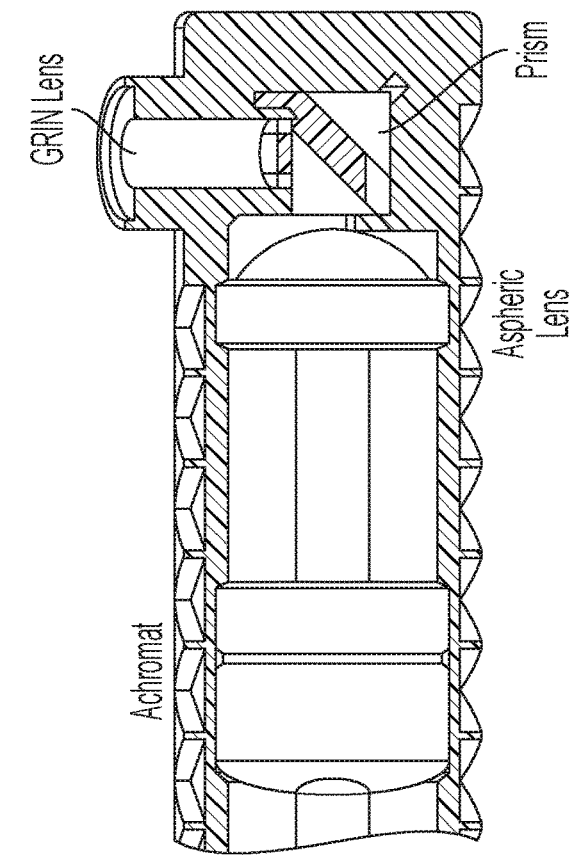
FIG. 5 is a schematic (left) of a probe housing and an image (right) of an assembled angle-dependent low-coherence interferometry probe, in accordance with aspects of the present disclosure.
Figure 5:
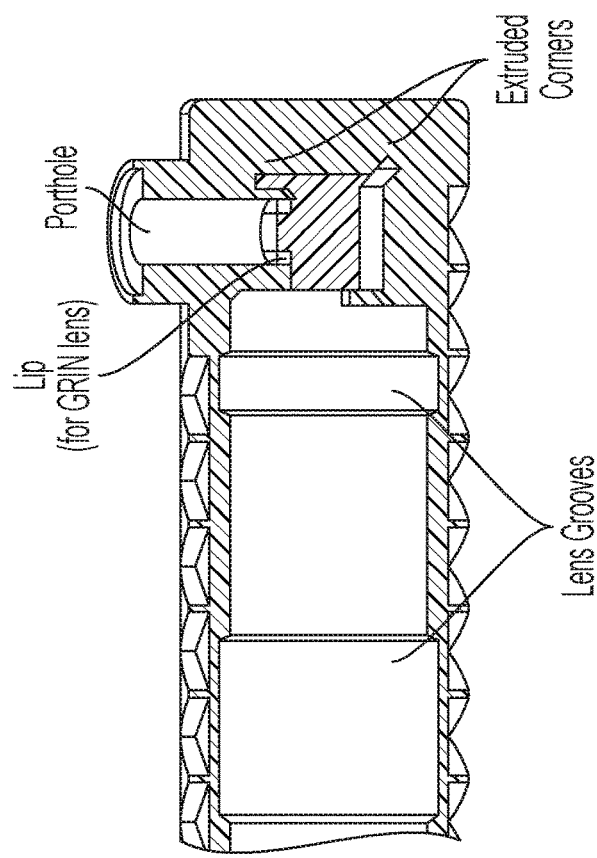

Referring to FIG. 5, a schematic for the plastic housing is shown (left) and a fully assembled probe is shown (right). For assembly, lenses were inserted in place, both halves were mated around the optics, then a no. 1 coverslip was bonded to the front surface of the GRIN lens, and the PLFA was inserted into the slot and held using set screws.

In one embodiment, the probe body was designed to hold the optical elements in place without the need for epoxy. This was achieved in practice by adding 50 mm of space to the exterior of each lens CAD file, and constructing a housing around the resulting surfaces. The probe body was fabricated in two halves which are joined for assembly, with sawtooth mating features to increase the surface area between halves for stronger bonding. A lip was added to support the GRIN lens on a portion of the proximal surface not used for imaging, and extruded cuts were added near corners of the prism to account for rounding of sharp features in the 3D printing process. A "porthole" feature was added to protect the GRIN lens from mechanical displacement.

In one embodiment, the PLFA was inserted into this ferrule to form the proximal end of the probe. Four 2.26 mm holes, threaded with a 4-40 tap hold the fiber array in place using set screws. The probe body was printed on a Form2 stereolithography 3D printer (Formlabs), with an outer diameter of 8 mm excluding the porthole and 9.6 mm including the porthole. This is comparable in size to modern gastroscopes (up to 12.9 mm) and smaller than radiofrequency ablation paddles (~10 mm) or comparable devices for esophageal OCT (11 mm).

Multi scale Imaging.

a/LCI measurements offer highly sensitive measurements of nuclear morphology which can be useful for assessing tissue health, including detection of pre-cancerous dysplasia for example. However, the need to reposition the probe for each measurement can limit clinical application. Further, the technique is non-imaging so it is not guided by visual data. This can also limit clinical application. In other aspects, the present disclosure further provides methods for combining a/LCI with imaging approaches that seeks to address these limitations.

Multiplexed Low Coherence Interferometry (mLCI).

According to one aspect of the present disclosure, the mLCI technique enables coherence imaging across a wide area of epithelial tissue, up to several cm in range. The approach uses multiple imaging spots in a two dimensional array. The detection uses spatial multiplexing, where multiple physical detection channels are present, and time multiplexing where each of the multiple detection channels are used to receive imaging data in sequence. The approach was initially used to assess thickness of microbicidal gels applied to the vaginal epithelium as an anti-HIV prophylactic approach.

In one embodiment, mLCI was used to examine the epithelium of the cervix. This probe incorporated 36 imaging points as an array of single mode fibers. An optical train imaged these 36 points on to the cervical mucosa using a triplet lens (L1) and a doublet lens (L2), while incorporating a meniscus lens at the distal end to enable imaging across the cervical mucosa. In this implementation two wedge prisms are incorporated to allow the probe to have a slight 8-degree bend to better conform to the anatomy. In practice this device is inserted into the vagina and the distal lens is placed in contact with the cervical epithelium. The probe includes a means for directly imaging the cervix, consisting of a means to deliver white light to the cervix, via optical fiber or direct illumination by an LED, and a means to collect that imaging using an imaging fiber bundle or by direct imaging using a miniature board level camera (CCD or CMOS).

This clinical study with this probe acquired 36 mLCI A-scans at widely sampled points across the cervical epithelium, covering approximately a 20 mm×20 mm field of view. The data were compared to physician labeled demarcation of squamous ectocervix and columnar endocervix. These data were used as input to develop a linear discriminant analysis (LDA) approach to automatically distinguish the two types of epithelium. The approach performed well in cases where there was sufficient mLCI signal to enable a measurement, as governed by SNR level, and there was adequate co-registration of the video image to enable physician labeling of epithelium type. Only 343 out of 1152 A-scans showed sufficient quality for analysis with other scans not producing good contact with the epithelium. Of the analyzed points 97.2% of ectocervix points were correctly identified by the analysis and 81.7% of the endocervix points were correctly identified. Although the performance was modest, there was a learning curve needed to gain expertise in applying the probe with greater performance as the study progressed. The data were useful in pointing the way towards an automated analysis of the cervical mucosa for epithelium type.

Figure 6:
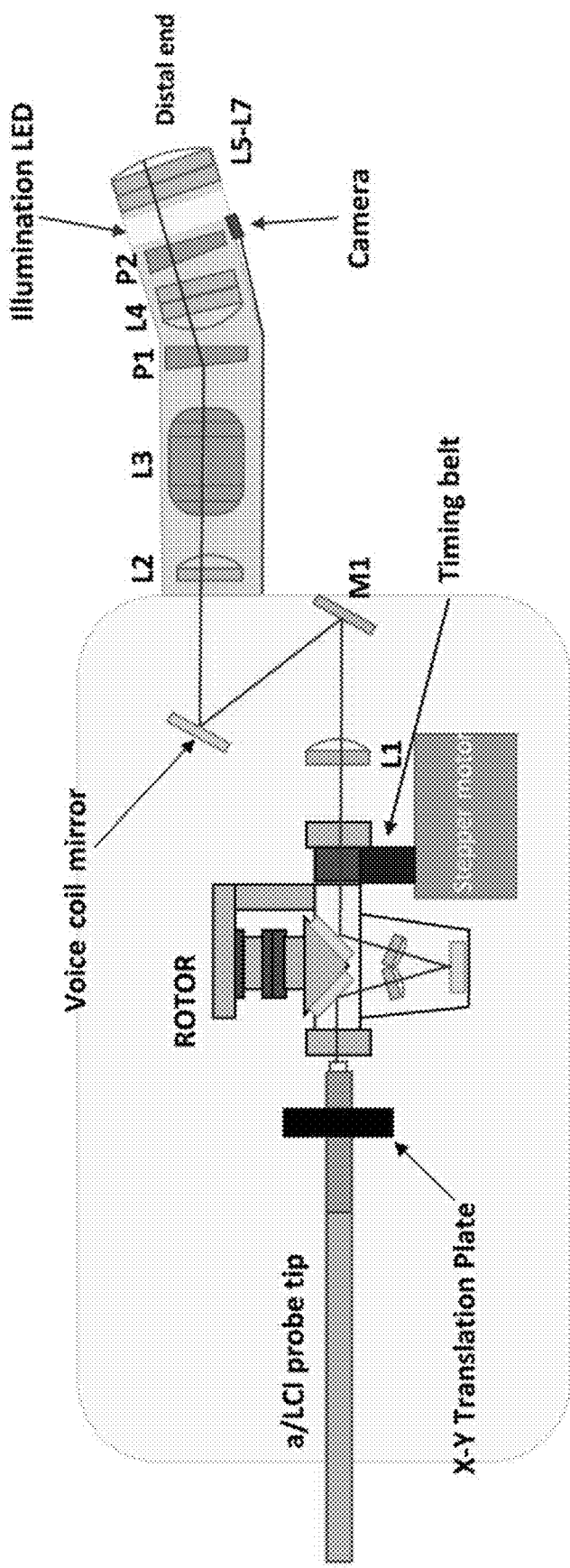
FIG. 6 is a schematic of the optical arrangement described with reference to cervical examination and in Example 1.

Referring to FIG. 6, a schematic of the cervical probe is shown. The same or similar probe was utilized for the cervical experiments described herein.

Integrated a/LCI Scans for Guidance.

To implement automated scanning, a commercial voice coil mirror (MR-15-30, Optotune) was used. This mirror was chosen for desirable properties including a small form factor, high mechanical tilt angle, and near-gimbal rotation. An aspheric lens L1 with high numerical aperture (NA=0.50) and short focal length (f=20 mm) was placed after the final ROTOR GRIN lens to minimize spherical aberrations while confining the optical fields to the diameter of the fold mirror M1 and voice coil mirror. A Hastings triplet L2 was placed after the scanning mirror in order to refocus the fields while collimating the off-axis rays and reducing spherical aberrations. Two doublet lenses (L3, L4) relay the fields to the end of the probe, arranged to minimize the axial focus shift between paraxial and off-axis rays. A doublet (L5) lens and double-concave (L6) lens are further used to optimize field collimation and minimization of spherical aberrations. A curved meniscus lens L7 was placed at the distal end to achieve contact imaging to match the curvature of the cervix while broadening the radius of the lens aperture used to maximize the angular collection range of the device. Additionally, two wedge prisms (P1, P2) are incorporated to create an 8-degree bend in the probe to allow it to conform to the anatomy of the vaginal canal.

A transverse scan using the voice coil mirror can take as little as 10 milliseconds to cover 20 degrees of tilt, corresponding to up to 20 mm across the tissue surface. After each mirror scan, the ROTOR is repositioned and another scan is implemented, creating an asterisk pattern. Although a/LCI data can be acquired at high speeds, it can take up to 200 msec to analyze each point so comprehensive a/LCI analysis of a broad tissue area is not feasible if the goal is to provide real time feedback for clinical diagnosis. Instead, this system can be operated in a fast scan mode where a/LCI scans are integrated across angle and simply presented as A-scans. This operation is fairly quick, enabling A-scans to be presented in real time. Thus, this system can be operated similarly to an mLCI system where sparse A-scans can be used to characterize broad tissue areas. The density of these A-scans is controlled by the acquisition rate of the sensor in the a/LCI system relative to the scan rate of the voice coil mirror. As an alternative, faster scans can be enabled by using the delivery fiber of the a/LCI system can also be used to collect direct backscatter and fed to a separate interferometer using an optical circulator. The backscattered light is then interfered with a reference beam to generate interference which is detected using a spectrometer with a fast line scan array (up to 80 kHz, for example). This provides A-scan data at a faster rate than the a/LCI sensor and would enable OCT imaging at a rate limited only by the scanning of the voice coil mirror when creating B-scans and by the ROTOR rotation rate to create volumetric (C-Scan) images.

A motor and pulley system rotates the ROTOR to rotate the imaging plane. A limit switch is used to home the ROTOR prior to scanning. The a/LCI imaging bundle is inserted into the rear of the device to couple with the interferometer and sensing system. The a/LCI probe is mounted on a miniature X/Y translation stage for alignment with the optical train.

This implementation can economize measurements taken by first mapping the surface of tissue during a preliminary scan that saves time and computational bandwidth by not utilizing the full angular range of a/LCI. Instead, only the back-scattered (0 degrees) light is collected and analyzed to form a 3D profile of the tissue, as in optical coherence tomography (OCT). The OCT data may be analyzed by the human operator or by automatic algorithm to determine the positions most suitable for a/LCI measurement, for example by identifying anatomical features known to be associated with higher risk of dysplasia. The a/LCI scanning can then be focused onto those selected positions for the previously described nuclear sizing measurements that are sensitive biomarkers for cancer and pre-cancer.

Combined OCT and a/LCI for Scanning Esophageal Epithelium.

The benefits of using OCT to target a/LCI scans have been discussed previously. Briefly, this combination overcomes the limitations of a/LCI not providing visual guidance. OCT imaging can provide insight into histological structures probed by a/LCI while also giving feedback on tissue orientation.

In one embodiment, the system comprised a benchtop system that permitted sequential OCT and a/LCI scans of a sample by using a flip mirror to switch between modalities. We now discuss a system designed to allow OCT and a/LCI to be applied to the same tissue location in vivo. The approach is implemented as an attachment to an upper GI endoscope to allow examination of the epithelium of the esophagus. The endoscope allows visual guidance to regions of interest in the esophagus which can be then examined in higher detail using the combined a/LCI and OCT probe.

FIG. 2 shows a schematic of the form factor for the probe in accordance with one embodiment of the present disclosure. The optical modalities are enclosed in a plastic housing (paddle) which is then mounted to the exterior tip of the endoscope using a flexible cuff. This configuration avoids the significant space limitations of introducing an imaging modality through the biopsy channel of the endoscope, as is done with many OCT implementations and commercial systems such as the Miniprobe from Cellvisio for confocal microscopy. To enable simultaneous application of both a/LCI and OCT, different spectral regions were chosen. a/LCI is traditionally centered around 840 nm since lower wavelengths are beneficial for conducting analysis of nuclear morphology. However, this need is balanced by the decrease of scattering and absorption at near infrared wavelengths. In this implementation, the OCT light is centered at 1310 nm. Inclusion of these two wavelengths, requires some design consideration. For example, the window of the paddle is anti-reflection coated that minimizes reflections at both 840 nm and 1310 nm.

The OCT and a/LCI probes are introduced through a channel in the paddle which is sheathed with a ETFE polymer to implement a water tight seal. The OCT probe here is a rotating fiber-optic design, consisting of a gradient-index (GRIN) lens and prism on the distal end, wound steel torque coil, a polymer sheath, and a fiber-optic rotary junction (FIG. 10). This probe can also be translated along the direction parallel to the endoscope to implement a pullback scan. The combination of the rotary and pullback scans can be used to generate volumetric scans.

The a/LCI modality is introduced to the paddle probe using a second channel. The a/LCI probe developed previously is approximately 2 mm in diameter and can fit alongside the OCT modality within the probe. The a/LCI probe can be adapted for side viewing using a prism and lens system similar to that described above for the single mode a/LCI fiber probe. The pathlength matched fiber array (PLFA) used in that probe can also be adapted for inclusion in the combined a/LCI and OCT probe. Since the probe for the PLFA is already side viewing, it can be included alongside the OCT probe in the paddle format. Alternatively, since the housing for the PLFA probe is 3D printed from the same material, it can also be modified to have an outer housing similar in shape to the paddle probe. Once included in the probe, the a/LCI modality can be operated in a pull back scan to conduct nuclear morphology measurements at points indicated in the OCT scan. In this configuration, the OCT modality is integrated into the probe by introducing a second small channel. Both modalities can be operated in pullback mode to conduct broad area scans of tissue using both modalities in tandem. As noted above, OCT provides imaging data at a faster rate than a/LCI analysis is executed. For this reason, the instrument is more efficiently operated by using real time feedback from the OCT images and then executing a/LCI analysis at points of interest, for example those suspected of harboring dysplasia.

Combination with Radiofrequency Ablation.

This probe housing form factor offers a significant advantage in that it is easily introduced endoscopically, and is similar to the form factor used for radiofrequency ablation (Barrx Halo 60 or Halo 90), the current most common treatment approach for Barrett's esophagus with dysplasia. Inclusion of OCT and/or a/LCI in a paddle housing that is also equipped for delivering radio frequency ablation can enable a 'see and treat' paradigm where tissue is examined for disease and then treated in a single procedure. In this case, the OCT and/or a/LCI modality is used to position the paddle over tissue sites that may harbor dysplasia. The imaging modality is then used to confirm the health status of the tissue. Therapeutic action can then be immediately taken once the presence of dysplasia has been identified. This approach offers a significant advance over the current clinical approach, which is to obtain biopsies of the esophageal epithelium, and then, if dysplasia is found, to perform a second procedure to allow treatment of the dysplastic areas. By potentially obviating the need for biopsies and a subsequent second endoscopic procedure, this device may markedly decrease the costs and risks associated with the treatment of precancerous conditions of the esophagus.

EXAMPLES

Example 1

Example 1 is briefly discussed above and is discussed in complete detail in Kendall et al., *Biomedical Optics Express*, Vol. 11, No. 9, Sep. 1, 2020, which is incorporated herein in its entirety by reference for all purposes.

Example 2

Example 2 is described primarily in the context of OCT imaging, but multimodal imaging is expressly contemplated and described in various aspects. This Example is combinable with all aspects of the disclosure described above, unless the context clearly dictates otherwise.

We used OCT to provide cross-sectional images of the esophageal epithelium. The technical details of the system are provided below. Briefly, an OCT system illuminates a sample with a beam of light. The depths of all reflections from a sample are determined using interferometry to produce a depth profile. Depth profiles are compiled into images by scanning the location of the beam on the sample, producing a 2D image in a manner similar to ultrasound.

Fiber optics contained in a custom sheath and paddle assembly were attached to an upper GI endoscope. A steel cable within the sheath turned the optical fiber assembly to produce images. Our OCT interferometric instrumentation was contained in a portable steel cart.

The probe was paddle-shaped and designed to be attached to the tip of the endoscope (FIG. 3). The housing was 3D printed using a biocompatible dental-grade resin (FormLabs, Somerville, MA). A flexible cuff for attachment to the endoscope was 3D printed using silicone (Carbon 3D, Redwood City, CA). An anti-reflective rectangular sapphire optical window (Guild Optics, Amherst, NH) was attached to the paddle. Biocompatible silicone (Masterbond, Hackensack, NJ) was applied to seal seams between components.

During the course of the study, three versions of the paddle were created (FIG. 3). Initially (FIG. 3—design a), the paddle was symmetric and included a tapered shape to facilitate articulation. In the subsequent design (FIG. 3—design b), modified in response to feedback from the endoscopist (NS), the front edge of the paddle was shortened and rounded to facilitate navigation of the probe through the upper esophageal sphincter (UES). The tapered shape at the proximal end of the paddle was deemed unnecessary, and was instead flattened to improve mechanical protection of the fiber optic probe within. In a final design iteration, we further revised the geometry of the probe to allow future use as a multimodality probe that would include additional optical elements to enable use of a/LCI. We reduced the thickness and increased the length of the probe, while placing the OCT optics off-center (FIG. 3—design c).

Human subjects research was conducted with approval from the Institutional Review Boards at Duke University Health System (Pro00090173) and the University of North Carolina (17-3037).

Subjects were recruited from patients undergoing routine care endoscopy at UNC Healthcare. Patients between the ages of 18 and 80 years presenting for upper endoscopy were eligible if one of the following criteria was satisfied: 1) No history of gastroesophageal reflux disease (GERD) or other esophageal condition affecting the epithelium, and without esophageal symptomology (including heartburn, globus, chest pain, dysphagia, and odonophagia); 2) Current dysplastic or non-dysplastic Barrett's esophagus of any length; or 3) History of dysplastic or non-dysplastic Barrett's esophagus after successful treatment with endoscopic eradication therapy (EET). Exclusion criteria included prior esophageal surgery (excepting uncomplicated Nissen fundoplication), pregnancy, inability to provide written informed consent, and a history of esophageal stricture or prior esophageal dilation.

To begin an imaging session, the endoscopist placed the silicone cuff over the tip of the endoscope similar to the placement of a focal RFA catheter, and navigated the probe into the esophagus under video guidance. The tip of the paddle was visible in the video endoscopy field of view, and was used to visually guide the OCT imaging location. For subjects with suspected regions of Barrett's esophagus or dysplasia, at least one OCT scan was acquired by placing the imaging window against the abnormal tissue, and commencing an imaging sequence of 10 to 15 frames. For all subjects, at least one such OCT scan was also acquired from a region of apparently healthy squamous epithelium. Following imaging, the endoscope was withdrawn. If biopsies were acquired as part of the patient's medical care from imaged regions, pathology results were obtained and added to the patient's research record to classify tissue types.

Our ability to discern BE from OCT was evaluated by comparing the image-based classification made by a human reviewer with the clinical diagnosis based on the pathology reading from a biopsy at the same location where available. Squamous tissue was differentiated from BE by endoscopic appearance, and confirmed histologically by the presence of specialized metaplasia demonstrating goblet cells. In some cases (2 patients), where a clinical biopsy was not obtained because immediate RFA rendered pre-treatment histology moot. In these cases, BE was classified based on visual findings consistent with BE and a previous history of histological samples demonstrating BE. 71 image sets were randomly ordered and presented to an OCT reader masked as to the clinical classification of the tissue, who classified the image sets into BE and normal categories. OCT interpretation was then compared to the clinical diagnosis and scored by its sensitivity and specificity to BE as well as overall classification accuracy.

The OCT system was a spectral-domain fiber-optic Michelson interferometer design (FIG. 2). Illumination was provided by a superluminescent diode (Exalos, Schlieren, Switzerland) centered at 1318 nm with a −3 dB bandwidth of 83 nm. The sample arm included a fiber-optic rotary junction (FORJ) (Princetel, Hamilton, NJ), which allowed rotation of the distal optics within the probe while remaining optically coupled to the stationary proximal sample arm. The FORJ was rotated using a mechanical coupling driven by a stepper motor (Teknic, Victor, NY). Optical and mechanical connection to the probe was accomplished via a rectangular SC-APC connector, which effectively transmitted driving torque directly to the connector. The probe shaft was a three-layer wound steel torque coil (Asahi Intecc, Seto-shi, Japan) surrounding a SMF-28 fiber. Distal optics, including a gradient-index (GRIN) objective lens and a prism, produced a focused beam in a side-viewing configuration that enabled tissue imaging through the probe window.

Light returning from the probe was combined with reference light and detected using a custom spectrometer. The spectrometer optics were modeled and optimized using optical design software (OpticsStudio, Radiant Zemax), and the physical components were designed using CAD software (Solidworks, Waltham, MA). The body of the spectrometer was 3D printed (Dremel 3D45) using Eco-ABS (Dremel, Racine, WI). The spectrometer sensor was an InGaAs linear array (Sensors Unlimited, Princeton, NJ).

Figure 7:
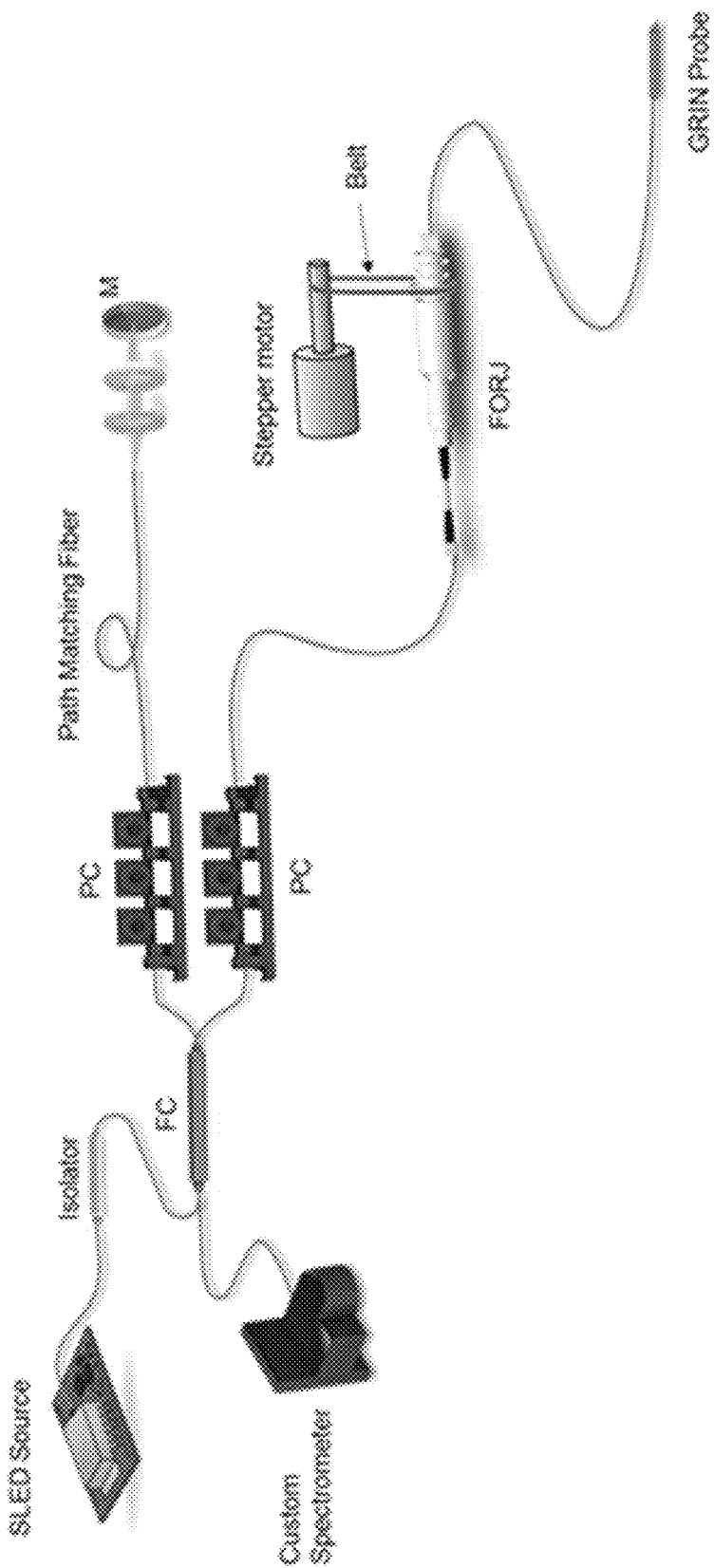
FIG. 7 is a schematic of the optical arrangement described in Example 2.

FIG. 7 shows an optical diagram. FC refers to fiber coupler. PC refers to polarization controller. M refers to mirror. FORJ refers to fiber optic rotary junction.

The OCT probe consisted of a single-mode optical fiber enclosed within a steel torque coil that transmitted the driving force of the probe. Optical connector epoxy was applied to secure the coil to the connector body on the proximal end, and to the fiber ferrule on the distal end. Two optical probe designs were used in this study, starting with a custom GRIN assembly built in-house, and progressing to another custom fabricated GRIN design assembled by the GRIN manufacturer (GRINtech, Jena, Germany).

In the first design, the distal optical fiber was terminated at a 1 mm glass ferrule (Accu-Glass, St. Louis, MO). The ferrule face was polished by clamping the ferrule into a bare fiber FC/APC adapter with a 1 mm bore and using a motorized fiber polisher (KrellTech, Neptune City, NJ), resulting in a reflection-minimizing 8-degree angle polish. The ferrule was then inserted into a steel hypotube segment with a small hole machined into its side. The GRIN objective lens was placed into the tube leaving 0.44 mm of space between the GRIN and the ferrule, a distance determined by optical modeling to achieve the desired working distance. The ferrule-GRIN gap was filled in with optical adhesive (Norland Products, Cranbury, NJ) for index matching. Finally, a right angle prism (Edmund Optics, Barrington, NJ) was attached to the GRIN with optical adhesive for a side-viewing configuration.

Despite the use of index matching optical adhesive between probe surfaces, there were still significant artifacts due to reflections in this first design. This limitation prompted an optical redesign during the clinical study. In the second design, a custom GRIN optical assembly was commissioned to be fabricated by GRINtech, with the prime objective of eliminating the gap between the ferrule and the GRIN. This was achieved by utilizing a GRIN element greater than 0.25 pitch in length, bringing the fiber illumination to a converging focus without need for a spacer. The factory-made elements also included an additional angle-polished interface between the GRIN and the prism, further eliminating specular reflections within the probe.

Standard spectral-domain OCT imaging techniques were employed to process raw interferometric data into 2D depth profiles (B-scans), including background subtraction, k-space interpolation, and dispersion compensation. See, for example, Wojtkowski, M., et al., *Ultrahigh-resolution, high-speed, Fourier domain optical coherence tomography and methods for dispersion compensation.* Optics express, 2004. 12(11): p. 2404-2422, which is incorporated herein in its entirety by reference for all purposes.

Because the OCT scan is rotational, the B-scans derived from our images were natively in polar coordinates. Non-uniform rotational distortion (NURD) caused a non-constant angular velocity that required correction using a custom procedure. First, we identified 8 key positions on the polar B-scan. In cross-section, the walls of the paddle cavity and the surface of the tissue form a rectangle; four key positions are the centers of each side, and the remaining four are the corners of the rectangle. Then, we estimated the true angular position of each A-line by using spline interpolation with the identified A-line positions as inputs and the known angular positions of those corresponding landmarks as outputs. Finally, we shifted these A-lines to conform to a linear angular ramp, and interpolated the B-scans in the angular dimension to smoothly fill the gaps. The polar coordinate images were then remapped to rectilinear coordinates and cropped.

We recruited 54 patients into the esophageal OCT imaging study. One patient was withdrawn due to inadvertent enrollment despite reporting an exclusionary symptom (heartburn). Of the 53 remaining, the probe was successfully navigated into the esophagus of 37 patients, of which 30 yielded adequate image sets, and 7 experienced technical failures. Table 1 below summarizes the patient enrollment.

TABLE 1

Patient enrollment summary

| Category | Successfully passed | Successfully imaged |
|---|---|---|
| Total number | 37 | 30 |
| Male | 32 | 28 |
| Female | 5 | 2 |
| Mean age | 65.5 years | 65.2 years |
| Age range | 24 – 80 years | 24 – 78 years |
| No current BE | 28 | 23 |
| Current BE | 9 | 7 |
| Non-dysplastic BE or indefinite for dysplasia | 8 | 6 |
| Dysplastic BE | 1 | 1 |
| Length of BE (Mean ± SD) | 5.1 ± 3.7 cm | 5.6 ± 3.9 cm |

The majority of data was obtained using our in-house designed and fabricated GRIN probe (22 imaged patients.) Representative images can be provided to a patent examiner if needed and public readers can locate a journal article describing this example for those images. Although image quality was generally adequate, internal reflections within the probe resulted in several bright line artifacts in the cross-sectional images. We minimized the overlap of the reflection artifact on key features of the image where possible, but unpredictable shifts in the visualized location of the tissue did occasionally result in unavoidable obscuration of portions of the image by the artifact.

The second probe, designed with all angle-polished surfaces, substantially removed the reflection artifacts. The modified design was employed for the final eight patients imaged in this study. Representative images generated by this version of the probe demonstrate the reduction in reflection artifacts and can be provided to a patent examiner if needed and public readers can locate a journal article describing this example for those images.

Our initial paddle design was utilized for only three patients, which were all successfully intubated, although only one resulted in usable images. Based on this experience with these cases, the clinician noted that a rounded front would be preferred for navigation past the UES to prevent catching on the sphincter. We therefore produced a second design that implemented a more snub-nose shaped, rounded anterior. Additionally, we noted that the degree of articulation permitted by the first design resulted in mechanical failures within the GRIN probe, which caused the technical failures in two of the three experiments. Our second design also incorporated a rigid metal hypotube segment to prevent excessive bending at the most vulnerable point of the optics.

The second paddle design was used for 23 imaging attempts, which resulted in 16 successful intubations (69.6%). The enhanced protection of this design prevented damage to the probes, and 13 successful imaging sessions. The third and final paddle design was used for 27 imaging attempts, 18 of which were successful intubations (66.7%), and 16 patients with successful image acquisitions.

Table 2 shows the results of the classification of random-ordered deidentified OCT images by a reviewer compared with the clinical diagnosis.

TABLE 2

Number of images classified Barrett's vs. non-Barrett's by OCT image vs. clinical diagnosis

|  | Clinical: Barrett's | Clinical: Non-Barrett's |
| --- | --- | --- |
| OCT: Barrett's | 11 | 4 |
| OCT: Non-Barrett's | 2 | 54 |

The OCT classification of BE was 91.5% accurate overall (65/71 image regions). Sensitivity for BE was 84.6% for BE (11/13) and specificity was 93.1% (54/58).

The primary aim in this work was to establish the feasibility of conducting OCT imaging of regions of esophageal epithelium selected by an endoscopist using a paddle probe mechanically coupled to the external housing of the endoscope. We were able to successfully image the majority of patients attempted and acquired high-resolution OCT images from the esophageal epithelium. Clear differences between squamous epithelium and Barrett's esophagus were observed, demonstrating that paddle probe OCT can be an effective means of distinguishing these conditions. The penetration depth afforded by 1300 nm OCT enabled visualization of the epithelium, lamina propria, muscularis mucosa, and submucosa.

The paddle probe format suggested here can provide several advantages. First, an endoscopist can readily direct the imaging to a specific location during the endoscopic procedure, allowing quick imaging of a particular region of interest without requiring a full volumetric scan or the introduction of a new imaging probe during the procedure. Secondly, attaching the probe externally to the endoscope allows the instrument channel to remain free, such that other through-the-scope interventions are feasible. Thus, the endoscopist can readily image a region of interest and directly follow up with a biopsy without the need for exchanging instruments in the channel. Finally, a paddle format is amenable to future adaptation for multimodality imaging and treatment. The final probe used in this study demonstrated that we could maintain comparable performance in a paddle form factor that included space to integrate a second optical modality, such as a/LCI. Additionally, this form factor was selected to allow potential implementation of a "see-and-treat" paradigm with endoscopic eradication therapy using the same paddle. Such an approach would enable the collapse of two episodes of care into a single endoscopy, and omit the costs associated with histological processing of biopsy specimens.

While our imaging approach does not provide a comprehensive volume image of the esophagus, the probe can be easily targeted to any region deemed suspect by the endoscopist, and can rapidly acquire images over multiple areas. Currently, this probe can be used to distinguish BE from squamous tissue by appearance on OCT. Classification accuracy using OCT was high overall, though possibly limited by the lack of exact registration between OCT scan locations and biopsy sites. While differentiation of squamous from BE tissue is not clinically relevant, as endoscopists can generally easily differentiate between the two, it does provide proof of principle that this side-viewing probe yields interpretable mucosal images. Additionally, although we did not assess the ability of our OCT device to differentiate dysplastic from non-dysplastic BE in this proof-of-principle study, previous work demonstrates that OCT has utility for this indication. The qualitative features that distinguish these tissues may be recognized using artificial intelligence (AI) algorithms in the future.

Overall, imaging quality was very good, and imaging success rate was high after some initial mechanical failures of the optical probe. Reflection artifacts were substantially reduced using probes assembled by GRINtech, demonstrating the importance of angle-polishing of internal components joined by optical adhesive. This improvement was evident qualitatively, as image-disrupting reflections were visibly reduced.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

We claim:

1. A system for multi-modal imaging using an endoscope having an instrument channel, wherein the multi-modal imaging is achieved without using the instrument channel, the system comprising:
- an endoscope selected from the group consisting of an anoscope, a colonoscope, a colposcope, an esophagoscope, a gastroscope, a laryngoscope, and a sigmoidoscope, the endoscope having a video camera positioned at a distal end for providing video images;
- a multi-modal imaging paddle housing coupled to the distal end of the endoscope, the multi-model imaging paddle housing occupying a retracted position adjacent to the distal end of the endoscope, the multi-modal imaging paddle housing optionally adapted to be movable between the retracted position and an extended position that is extended axially and/or radially from the distal end of the endoscope, the multi-modal imaging paddle housing adapted to receive a portion of at least two imaging probes, the multi-modal imaging paddle housing having a single imaging window, through which each of the at least two imaging probes acquire images, or two imaging windows, each through which a respective one of the at least two imaging probes acquires images;
- an angle-resolved low-coherence interferometry (a/LCI) probe having at least a distal portion received within the multi-modal imaging paddle housing;
- an optical coherence tomography (OCT) probe having at least a distal portion received within the multi-modal imaging paddle housing; and
- an imaging controller operatively coupled to the a/LCI probe and the OCT probe,
- wherein the multi-modal imaging paddle housing has a shape and a location in the retracted position, wherein the shape and the location combine to make the multi-modal imaging paddle housing visible in the video images provided by the video camera, such that a user can visually guide the multi-modal imaging paddle housing to a region of interest,
- wherein the a/LCI probe and the OCT probe are electronically coupled to the imaging controller and optically coupled to respective light sources and optical detectors via wires and optical fibers that are coupled to an exterior surface of the endoscope,
- wherein the a/LCI probe operates within a first wavelength range and the OCT probe operates in a second wavelength range, wherein the first and second wavelength ranges are different and non-overlapping, wherein the single imaging window transmits at least 95% of light at each wavelength in the first wavelength range and the second wavelength range, wherein one of the two imaging windows transmits at least 95% of light at each wavelength in the first wavelength range, wherein the other of the two imaging windows transmits at least 95% of light at each wavelength in the second wavelength range,
- wherein the instrument channel is not occupied by the a/LCI probe or the OCT probe.

2. The system of claim 1, wherein the multi-modal imaging paddle housing further comprises one or more radiofrequency ablation electrodes, wherein the one or more radiofrequency ablation electrodes are coupled to external power and controls via the wires that are coupled to the exterior surface of the endoscope.

3. The system of claim 1, wherein the multi-modal imaging paddle housing including a coupling cuff and is coupled to the distal end of the endoscope via the coupling cuff.

4. The system of claim 1, wherein the first wavelength range includes 840 nm within it and the second wavelength range includes 1310 nm within it.

5. The system of claim 1, wherein the a/LCI probe includes a reflection-only three-optic rotator prism and a two-axis scanning mirror.

6. The system of claim 5, wherein the controller is adapted to direct the a/LCI probe and the respective light sources and optical detectors to acquire A-scans by varying an angle of the reflection-only three-optic rotator prism.

7. The system of claim 1, wherein the a/LCI probe is coupled to the respective light sources and optical detectors via a pathlength-matched linear fiber array comprising a plurality of single-mode optical fibers, via coherent fiber bundles, or via a single multi-mode fiber.

8. The system of claim 1, wherein the OCT probe is a rotating probe.

* * * * *